United States Patent [19]
Imam et al.

[11] Patent Number: 5,851,830
[45] Date of Patent: Dec. 22, 1998

[54] LUMINAL EPITHELIAL ANTIGEN

[75] Inventors: S. Ashraf Imam, N. Hollywood; Clive R. Taylor, South Pasadena, both of Calif.

[73] Assignee: University of Southern California, Los Angeles, Calif.

[21] Appl. No.: 412,833

[22] Filed: Mar. 29, 1995

Related U.S. Application Data

[63] Continuation of Ser. No. 33,672, Mar. 16, 1993, abandoned.
[51] Int. Cl.$^6$ .......................... C07K 16/18; C07K 16/28; C12N 5/20; C12N 5/18
[52] U.S. Cl. .......................... 435/334; 435/346; 436/548; 530/388.22; 530/388.2; 530/389.1; 530/809; 935/89; 935/95; 935/104
[58] Field of Search ..................................... 435/7.1, 7.23, 435/975, 240.27, 334, 346; 436/813, 548; 530/388.22, 388.85, 389.1, 350, 395, 388.2, 809; 935/89, 95, 104

[56] References Cited

PUBLICATIONS

I.U. Ali et al., "Reduction to Homozygosity of Genes on Chromosome II in Human Breast Neoplasia", *science*, 238:185–188 (9 Oct. 1987).
Baker et al., "Chromosome 17 Deletions and p53 Gene Mutations in Colorectal Carcinomas", *Science*, 244:217–221 (14 Apr. 1989).
Chen et al., "Loss of Heterozygosity on Chromosome 1q in Human Breast Cancer", *Proc. Natl. Acad. Sci USA*, 86:7204–7207 (Sep. 1989).
Eliyahu et al., "Wild–Type p53 Can Inhibit Oncogene–Mediated Focus Formation", *Proc. Natl. Acad. sci. USA*, 86:8763–8767 (Nov. 1989).
Fearon et al., "Identification of a Chromosome 18q Gene That Is Altered in Colorectal Cancers", *Science*, 247:49–56 (5 Jan. 1990).
Friend et aql., "Oncogenes and Tumor–Suppressing Genes", *New England J. of Med.*, 318:618–622 (Mar. 10, 1988).
Friend et al., "a Human DNA Segment With Properties of the Gene that Predisposes to Retinoblastoma and osteosarcoma", *Nature*, 323:643–646 (16 Oct. 1986).
Fung et al., "Structural Evidence for the Authenticity of the Human Retinoblastoma Gene"., *Science*, 236:1657–1661 (26 Jun. 1987).
Imam et al., "Generation and Immunohistological Characterization of Human Monoclonal Antibodies to Mammary Carcinoma Cells", *Cancer Research*, 45:263–271 (Jan., 1985).
Imam et al., "Identification of a Cell–Surface Antigen (LEA.135) Associated with Favorable Prognosis in Human Breast Cancer", *Cancer Research*, 53:3233:3236 (Jul. 15, 1993).
Imam et al., "application of Immunohistochemical Methods in the Diagnosis of Malignant Disease", *Cancer Investigation*, 3(4):339–359 (1985).
Imam et al., "Generation and Characterization of a Murine Monoclonal Antibody to Cervical Glandular Epithelium Using Mice Rendered Tolerant to Cervical Squamous Epithelium", *Hydbridoma*, vol. 9, No. 2, pp. 157–166 (1990).
Knudson, Jr., Alfred G., "Hereditary Cancer Oncogenes and Antioncogenes", *Cancer Research*, 45:1437–1443 (Apr. 1985).
Lee et al., "Human Retinoblastoma Susceptibility Gene: Cloning, Identification and Sequence", *Science*, 235:1394–1399 (13 Mar. 1987).
Lubbert et al., "p53 in Chronic Myelogenous Leukemia", *J. Exp. Med.*, 167:873–886 (mar. 1988).
Lundberg et al., "Loss of Heterozygosity in Human Ductal Breast Tumors Indicates a Recessive Mutation on Chromosome 13", *Proc. Natl. acad. Sci. USA*, 84:2372–2376 (Apr. 1987).
Poppema et al., "Distribution of T Cell Subsets in Human Lymph Nodes", *J. Exp. Med.*, 153:30–40 (Jan. 1981).
Stein et al., "Immunohistologic Analysis of the Organization of Normal Lymphoid Tissue and Non–Hodgkin's Lymphomas", *J. of Histochemistry and Cytochemisty*, vol. 28, No. 8, pp. 746–760 (1980).
Stein et al., "Immunohistologic Analysis of the Organization of Normal Lymphoid Tissue and Non–Hodgkin's Lymphomas", *J. of Histochemistry and Cytochemistry*, vol. 28, No. 8, pp. 746–760 (1980).
Tubbs et al., "Tissue Immunomicroscopic Evaluation of Monoclonality of B–Cell Lymphomas", *Lymphoma Immuonohistochemistry*, vol. 76, No. 1, pp. 24–28 (1981).
Warnke et al., "Tissue Section Immunologic Methods in Lymphomas", *Diagnostic Immunohistochemisty* (DeLellis RA, editors) Masson, N.Y. (1981) pp. 203–211.
Weinberg, Robert A., "Oncogenes, Antioncogenes, and the Molecular Bases of Multistep Carcinogenesis ", *Cancer Research*, 49:3713–3721 (Jul. 15, 1989).
Godins, "Monoclonal Antibodies, Principles and Practices", Academic Press, 1986, pp. 59–103.
Imam et al., Anticancer Res. 12: 1806, 1992.
Imam et al., Breast Cancer Res and Treatment, 19: 157, 1991.
Imam et al., Cancer Res. 53(14), 3233–36, 1993.

*Primary Examiner*—Ronald B. Schwadron
*Attorney, Agent, or Firm*—Fulbright & Jaworski

[57] ABSTRACT

A cell-surface glycoprotein, termed luminal epithelial antigen, having a molecular weight of 135 Kd and which is present in normal mammary epithelial cell lines but not in malignant epithelial cell lines. A monoclonal antibody directed against said luminal epithelial antigen. Use of the monoclonal antibody in a diagnostic assay for the early identification of patients with high risk of developing breast cancer and in a prognostic assay for the prediction of recurrence of breast cancer in patients.

2 Claims, 4 Drawing Sheets

LUMINAL EPITHELIAL ANTIGEN

This is a continuation of Ser. No. 08/033,672 filed Mar. 16, 1993, now abandoned.

BACKGROUND OF THE INVENTION

The present invention relates generally to the fields of biochemistry and medicine. In particular, the present invention relates to a glycoprotein, termed luminal epithelial antigen (LEA.135), which is present in normal mammary epithelial cell lines but not in malignant epithelial cell lines, to a monoclonal antibody (anti-LEA.135) directed against the luminal epithelial antigen and to methods for the production and use of the antibody.

The hypothesis that inactivation of tumor-suppressor genes may play important roles in the development of human malignancies has recently received considerable attention [A. G. Knudson, Jr., "Hereditary Cancer, Oncogenes, and Antioncogenes," Cancer Res. 45:1437–1443 (1985); S. H. Friend et al., "Oncogenes and Tumor-Suppressing Genes," N. Engl. J. Med. 318:618–622 (1988); R. A. Weinberg, "Oncogenes, Antioncogenes, and the Molecular Basis of Multistep Carcinogenesis," Cancer Res. 49:3713–3721 (1989)]. To date, three such suppressor genes, namely retinoblastoma (RB1) [S. H. Friend et al., "A Human DNA Segment with Properties of the Gene that Predisposes to Retinoblastoma and Osteosarcoma," Nature 323:643–646 (1986); W-H. Lee et al., "Human Retinoblastoma Susceptibility Gene: Cloning, Identification, and Sequence," Science 235:1394–1399 (1987); Y.-K. T. Fung et al. "Structural Evidence for the Authenticity of the Human Retinoblastoma Gene," Science 236:1657–1661 (1987)], p53 [M. Lubbert et al., "p53 in Chronic Myelogenous Leukemia," J. Exp. Med. 167:873–886 (1988); and D. Eliyahu et al., "Wild-type p53 Can Inhibit Oncogene-Mediated Focus Formation," Proc. Natl. Acad. Sci. USA 86:8763–8767 (1989); T. Takahashi et al., "p53: A Frequent Target for Genetic Abnormalities in Lung Cancer," Science 246:491–494 (1989)] and DCC genes [E. R. Fearon et al., "Identification of a Chromosome 18 q Gene That Is Altered in Colorectal Cancer," Science 247:49–56 (1990)], have been reported and their role in the suppression of retinoblastoma and colon tumor-growth documented.

Evidence for the loss or inactivation of tumor-suppressor genes in breast carcinomas comes from independent reports that describe allelic losses on several chromosomes, including 1q [L.-C. Chen et al., "Loss of heterozygosity on Chromosome 1q in Human Breast Cancer," Proc. Natl. Acad. Sci. USA 86:7204–7207 (1989)], 11 p [I. U. Ali et al., "Reduction to Homozygosity of Genes on Chromosome 11 in Human Breast Neoplasia," Science 238:185–188 (1987)], 13 q [C. Lundberg et al., "Loss of Heterozygosity in Human Ductal Breast Tumors Indicates a Recessive Mutation on Chromosome 13, " Proc. Natl. Acad. Sci. USA 84:2372–2376 (1987)] and 17 p [S. J. Baker et al., "Chromosome 17 Deletions and p53 Gene Mutations in Colorectal Carcinomas," Science 244:217–221 (1989)] in malignant cells from breast. Clearly, such gross chromosomal defects indicate loss of numerous genes, only a few of which may be important in the neoplastic process. Although relatively gross chromosomal defects have been observed, the precise genes involved have not been determined and their specific products have not been identified. Acting on the premise that biologically important growth control (suppressor) genes direct the synthesis of certain cell products (negative and/or suppressor growth factors), attempts were made to define these genes by first identifying their products, sequencing the amino acid residues of the products, synthesizing oligonucleotides based on the sequence information and using the oligonucleotides as probes in order to identify and subsequently clone cDNA sequences which encode the products.

Attempts were made to identify such products by means of generating monoclonal antibodies using a tolerization prior to immunization procedure designed to detect minute antigenic difference between malignant and normal cells of the same tissue [A. Imam et al., "Generation and Characterization of a Murine Monoclonal Antibody to Cervical Glandular Epithelium Using Mice Rendered Tolerant to Cervical Squamous Epithelium," Hybridoma 9:157–166 (1990)]. The procedure of immunization of mice with normal epithelial cell lines, following prior tolerization with breast carcinoma cells, favors the generation of antibodies to the products of normal cells. Using such a technique, a cell-surface glycoprotein, recognized by a newly developed monoclonal antibody generated by said technique, with an apparent molecular weight of 135 kD was identified. The glycoprotein has been termed luminal epithelial glycoprotein (LEA.135).

For the past two decades, efforts to find molecules that are specifically expressed on tumor cells and absent from their normal counterparts have met without success. Conversely, the absence in cancer cells of normal and functionally relevant molecules, which are functional in the maintenance of normal phenotype in breast offers new and promising approaches to: (1) early identification of patients with breast cancer and prediction of recurrence of breast cancer (diagnostic and prognostic use) and (2) reactivation of the expression of such molecules in tumor cells in order to reverse their malignant growth (e.g., gene therapy).

SUMMARY OF THE INVENTION

In accordance with a first aspect of the present invention, there is provided a 135 kd glycoprotein, which is present in normal mammary epithelial cell lines but not in malignant epithelial cell lines, termed luminal epithelial antigen (LEA.135).

In accordance with a further aspect of the present invention, there is provided a monoclonal antibody directed against a protein which is present in normal mammary epithelial cell lines but not in malignant epithelial cell lines.

In accordance with another aspect of the present invention, there is provided a method of using anti-LEA.135 in a diagnostic assay for the early identification of patients with high risk of developing breast cancer.

In accordance with another aspect of the present invention, there is provided a method of using anti-LEA.135 in a prognostic assay for the prediction of recurrence of breast cancer in patients.

In accordance with another aspect of the present invention, there is provided a method involving tolerization prior to immunization techniques for the production of monoclonal antibodies which are specifically directed against proteins which are present in normal mammary epithelial cell lines but not in malignant epithelial cell lines.

DETAILED DESCRIPTION OF THE INVENTION

Figure 1:
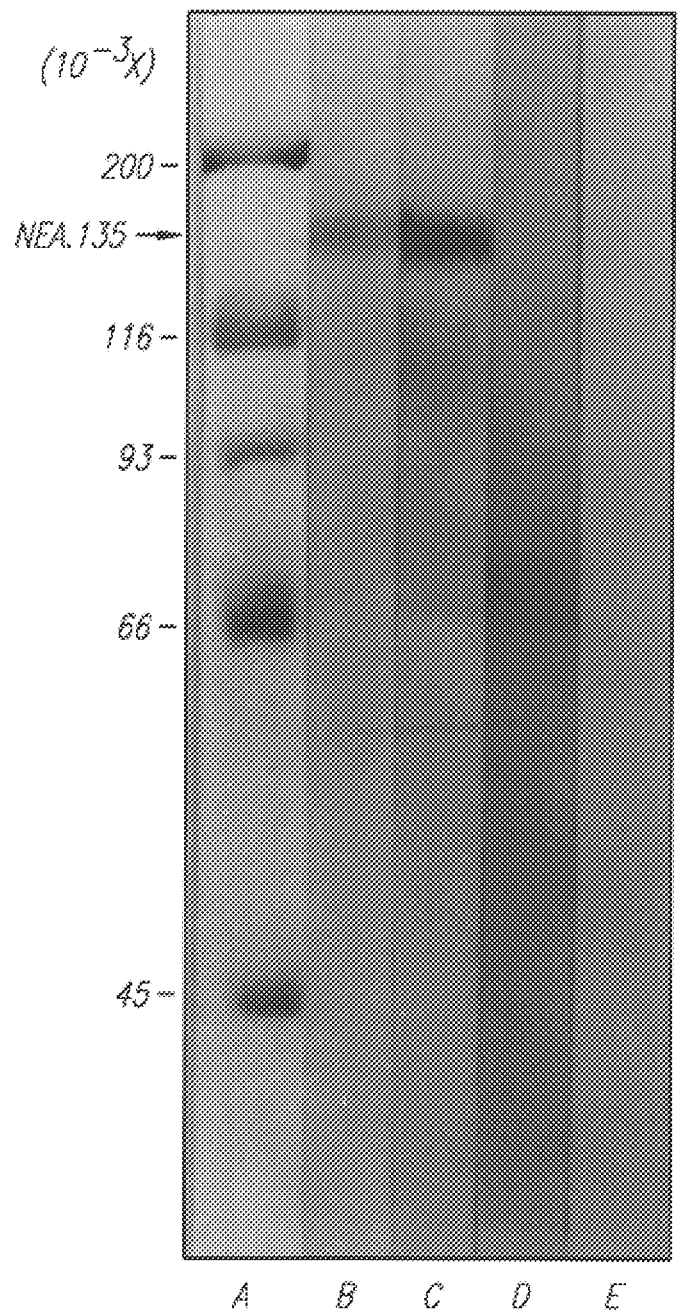
FIG. 1 is a sodium dodecyl sulphate-polyacrylamide gel electrophoretic analysis of the component immunoprecipitated by anti-LEA.135 monoclonal antibody.

In accordance with a first aspect of the present invention, there is provided a protein which is, to the limits of detection of the present technique, present in normal mammary epithelial cell lines but not in malignant epithelial cell lines. The protein (LEA.135) is characterized in that the sequence of the first eight amino acid residues in the N-terminus region is as follows: PELSAVYT [SEQ ID NO:1] (using the single letter amino acid code).

For purposes of claiming materials by designation, A56.7C2(0) hybridoma clonal cells were deposited on Dec. 22, 1992 with the American Type Culture Collection (ATCC), 12301 Parklawn Drive, Rockville, Md., 20852, under the provisions of the Budapest Treaty for the International Recognition of the Deposit of Microorganisms for the Purpose of Patent Procedure. These were tested by the ATCC on Dec. 30, 1992, and determined to be viable. The ATCC has assigned the deposit number HB 11225 to these materials. Hybridoma cell line A56.7C2 (a.k.a. HB 11225) produces anti-LEA.135 monoclonal antibody.

Immortalized (non-tumorigenic) or malignant (tumorigenic, MCF.7, MDA MB 231 or ZR 75) mammary epithelial cell (MEC) lines were grown as monolayer cultures in 75 mm$^2$ tissue culture flasks and intrinsically labelled when cultures were still subconfluent. The cells were labelled for 24 to 48 h with either 2 mCi of $^3$H-leucine or galactosamine (110 Ci mmol$^{-1}$) per flask of leucine or galactosamine-free DME medium respectively. Following incubation, the cells were washed three times and lysed with 0.05M Tris-HCl buffer, pH 7.5, containing 0.15M NaCl, 0.5% (v/v) Nonidet P-40 (NP-40), 0.5% (w/v) sodium deoxycholate, 1 mM phenylmethylsulphonyl fluoride and 0.5 mM choloromethyl-L-(2-phenyl-1-p-toluenesulphosnamide) ethyl ketone on ice for 15 min. The lysates were centrifuged at 40,000×g and 4° C. for 10 min. The supernatant containing detergent-solubilized materials was subsequently used for immunoprecipitation.

The radiolabelled cell lysates (approximately 400 ng of protein containing 5×10$^7$ c.p.m.) were mixed with 100 $\mu$l of either anti-LEA.135 antibody (0.1 mg ml$^{-1}$) or anti-LEA.135 antibody preabsorbed with the purified preparation of LEA.135. The latter antibody served as a negative control. The mixtures were incubated at 4° C. for 16 h. Following the incubation, a 100 $\mu$l suspension of Sepharose 4B (agarose, a purified linear galactan hydrocolloid) conjugated to goat antimouse immunoglobulins was added to each reaction mixture. The samples were incubated for a further period of 60 min and centrifuged at 5,000 ×g for 5 min. Following the removal of supernatant by aspiration, the pellet was washed five times with 0.05M NaCl, 1.0% (w/b) ovalbumin and 0.2% (v/v) NP-40 to remove any non-specifically bound radioactivity. No radioactivity was detectable in the supernatant of the fifth wash.

The materials immunoprecipitated with anti-LEA.135 antibody were subsequently analyzed by sodium dodecyl sulphate polyacrylamide gel electrophoresis (SDS-PAGE). The washed pellets were solubilized in 0.05M Tris-HCL buffer pH 6.8, containing SDS and 2-mercaptoethanol, boiled for 5 min and centrifuged at 8,000 g for 5 min at ambiant temperature. The supernatants were subjected to electrophoresis in 7.5% polyacyrlamide slab gels in the presence of SDS. A constant current of 30 mA was applied to each gel for approximately 4 h until the dye front approached to within 1 cm of the bottom. The gels were then fixed and stained with 0.25% (w/v) Coomassie blue in a solution containing 50% (v/v) isopropyl alcohol and 10% (v/v) glacial acidic acid. The destained gels were treated with "ENHANCE" (New England Nuclear, Boston, Mass.) polyoxyethylene sorbitan monolaurate, a non-ionic detergent and dried on a Whatman no. 3 MM filter paper under reduced pressure, and the radioactive components were visualized by fluorography.

$^3$H-leucine or $^3$H-galactosamine labelled cells from immortalized (non-tumorigenic) or malignant (tumorigenic) MEC were used to study the nature and specificity of expression of antigen recognized by anti-LEA.135 antibody. The immunoprecipitation experiments, using the NP40-deoxycholate solubilized lysates of intrinsically labelled components of the immortalized MEC, revealed that the antigen recognized by the antibody represented 0.007% of the total lysate. Autoradiographical analysis of $^3$h-leucine labelled immortalized MEC lysate on SDS-polyacrylamide gel electrophoresis showed one component with an apparent molecular weight of 135 kilodaltons. Furthermore immunoprecipitation of $^3$H-galactosamine labelled immortalized MEC lysate and the antibody yielded a component that migrated to the same position on the gel as did the $^3$H-leucine labelled 135 kd-component. The preabsorbed antibody failed to immunoprecipitate any detectable component from either $^3$H-leucine or $^3$H-galactosamine labelled lysated of the immortalized MEC. Conversely, lysates of the malignant cells were non-reactive with the antibody.

To investigate the nature of the antigen immunoprecipitated with anti-LEA antibody, $^3$H-leucine or $^3$H-galactosamine labelled immunoprecipitates were analyzed under both reducing and non-reducing conditions by SDS-PAGE. Under both conditions, patterns of migration of the component remained unchanged, suggesting the absence of disulphide bonds between the molecule.

This protein is characterized in that it is a cell surface glycoprotein with an apparent molecular weight of 135 kD and is recognized by a monoclonal antibody which is generated by use of a tolerization prior to immunization technique.

Tolerance to malignant mammary epithelial cell lines (MCF.7 or MBA.MD.231) was induced in neonatal mice (within 24 hr of birth), prior to subsequent immunization with an extract of normal breast tissue.

Within 24 hr after birth 11 Balb/c mice were "tolerized" by intraperitoneal (IP) injection of tolerogen (1 to 2 mg protein extract of malignant mammary epithelial cell lines). Twenty-four hours later, a second injection of the tolerogen was administered as above. Three weeks later, mice were bled from the tail vein and the sera were screened for lack of reactivity against the tolerogen. Two methods were employed in parallel, an enzyme-linked immunosorbent assay (ELISA), using the tolerogen as the target antigen, and an immunohistological method, using frozen-tissue sections of breast containing both normal and malignant mammary epithelial cells. Based on these assays, the sera of 5 mice showed no reactivity to tolerogen. These 5 mice were selected for immunization at age 3 weeks with the extract of normal mammary epithelial cell lines (immunogen). Such mice received the first injection of 0.2 mg protein extract (immunogen) in 50%, (v/v) complete Freund's adjuvant. Subsequently two booster immunizations with incomplete Freund's adjuvant were given at an interval of one a week. Three days after the last booster injection, the mice were again bled and sera were subjected to screening by the ELISA and immunohistological staining methods, this time using both tolerogen and immunogen to determine the efficiency of tolerization and immunization. Four mice showed evidence of serum antibodies reactive to normal mammary epithelial cell lines, but not to malignant epithelial cell lines; serum from the fifth animal showed a broad spectrum of reactivity against many cell types. Achievement of tolerance was evaluated by immunohistochemical methods, testing sera from mice against the tolerogen (MCF.7 or MBA.MD.231).

Normal and neoplastic tissues were obtained from the surgical pathology files of the Los Angeles County-University of Southern California Medical Center. Tissues were fixed in B5 or formalin, dehydrated, cleared and embedded in paraffin. Tissue sections were cut at five microns of thickness for Hematoxylin, Eosin and immunostaining.

An indirect unlabeled primary antibody method was used for localizing antigen with the specific antibody as described previously [A. Imam et al., "Application of Immunohistochemical Methods in the Diagnosis of Malignant Disease," Cancer Invest. 3:339–359 (1985)]. Biotinylated horse anti-mouse immunoglobulin was used as the link between the specific antibody and the avidin-biotin-peroxidase conjugate (ABC). Throughout this study, primary and secondary antibodies and ABC reagent were used at a constant concentration as determined by initial optimal titration analysis. Visual estimates of intensity of staining were scored as absence (−), weak (1+), moderate (2+), and intense (3+). To account for case-to-case variation in the intensity of staining, normal or neoplastic specimens were evaluated relative to a tissue section containing normal mammary epithelium which was scored as 3+, and served as a positive control. Visual estimates of the percentage of cells stained were determined by examining 5 different and random fields on every tissue section at high magnification (×400). The mean of count from the fields examined was used to arrive at the percentage of cells with staining. For each experiment, negative controls were performed to ensure the specificity of the reaction. These controls included the use of specific antibody following absorption with the immunogen, and irrelevant antibody of the same immunoglobulin class, in lieu of the specific antibody. Tolerized mice, showing absence of serum antibodies against the tolerogen, were subsequently immunized with extracts of breast tissue containing normal epithelial cell lines (immunogen). Evidence of antibody production was sought by contrasting positive reactivity for normal mammary epithelial cell lines with absence of reactivity for their malignant counterparts by the aforementioned immunohistochemical methods. The spleen cells from a mouse showing evidence of production of serum antibody with these characteristics, and strong reactivity, was subsequently used for hybridization and production of monoclonal antibodies.

One mouse, showing the strongest reactivity to normal mammary epithelial cell lines and absence of binding to malignant mammary epithelial cell lines was sacrificed. Spleen cells were purified and fused with mouse myeloma cells (M5, a nonsecreting variant of the mouse myeloma cell sub-line of SP2/OAg14) at a ratio of 3 to 1, respectively, using 34% (v/v) polyethylene glycol (M, 1,500) as described by Imam et al. [A. Imam et al., "Generation and Immunohistochemical Characterization of Human Monoclonal Antibodies to Breast Carcinoma Cells," Cancer Res. 45:263–271 (1985)]. Supernatants from wells showing hybrid growth were subject to screening by the ELISA method and subsequently by an indirect immunohistological method as described hereinabove. Hybrids from positive wells of 96-well plates were cloned by limiting dilution. When single clones had grown to about 70% confluence, supernatants from each well, exhibiting growth of a single colony, were again assayed for the presence of antibody reactive to immunogen, but not to tolerogen, as described herein above. Those hybrids finally selected were subjected to two further cycles of cloning by limiting dilution, a process that favors development of stable clones. One of these antibodies, designated anti-luminal epithelial antigen (anti-LEA.135), showing the strongest reactivity with the above properties, was selected for detailed studies. The initial screening of hybridoma supernatants was performed using freshly frozen tissue sections containing normal or malignant mammary epithelial cell lines by the immunohistological staining methods described hereinabove.

Solubilized tissue preparations containing antigen served as the basis for an ELISA type assay to detect the presence of specific monoclonal antibodies. Fifty $\mu$l of solubilized extract containing 1 mg of protein per ml were added to each "U" shaped well of a polyvinyl chloride microtiter plate (Dynatech, Alexandria, Va.) and incubated at 4° C. overnight. Following incubation, supernatants were aspirated and the wells were filled with 200 $\mu$l of 0.1M sodium carbonate-bicarbonate buffer, pH 9.6 (coating buffer), containing 1.0% (w/v) bovine serum albumin (RIA grade), to reduce nonspecific absorption of protein during the course of the assay. The plate was then incubated for 1 h at room temperature. The remainder of the experiment was carried out at room temperature. Fifty $\mu$l of spent medium containing, or suspected to contain, monoclonal antibodies were added in duplicate to the coated wells and incubated for 30 min. Fifty $\mu$l of an irrelevant monoclonal antibody was added to additional wells which served as negative controls. Following incubation, the medium was aspirated and the wells were washed three times with 0.01M sodium phosphate buffer, pH 7.2, containing 0.15M NaCl (PBS) and 0.05% (v/v) TWEEN 20 (PBS/TWEEN 20), which also served as the dilution buffer. Subsequently, 50 $\mu$l of alkaline phosphatase-labeled rabbit antimouse IgG or IgM (diluted 1:1,000 in dilution buffer) were added to the well. The plate was incubated for 30 min. The supernatants were aspirated, the wells were washed three times with the washing buffer and finally twice with distilled water. A substrate solution consisting of 100 $\mu$l 0.05M sodium carbonate buffer, pH 9.8, containing 1 mM $MgCl_2$ and 1 mg/ml P-nitrophenylphosphatase was added to each well and the reaction was continued for 15 to 30 min. The enzyme reaction was terminated by adding 100 $\mu$A of 0.5N NaOH in distilled water. Optical density of each reaction mixture was read at 410 nm in a spectrophotometer (EIA reader, Bio-Tek Instruments, Inc.). Supernatants containing antibodies with reactivity against many cell types in the tissue sections were rejected. A small number of wells with hybrids secreted antibody that showed strong reactivity with the normal cells, but lacked reactivity against mammary carcinoma cells in tissue sections. These hybrids were repeatedly subcloned, until one clone, producing consistently high levels of monoclonal antibody with the above properties, was selected for detailed study. This antibody was termed anti-luminal epithelial antigen (anti-LEA.135) to indicate its reactivity and an apparent molecular weight of the target antigen (FIG. 1).

FIG. 1 shows a sodium dodecyl sulphate-polyacrylamide gel electrophoretic analysis of the component immunoprecipitated by anti-LEA.135 monoclonal antibody. Component immunoprecipitated by the antibody and $^{125}$I-labelled lysate of the immortalized (non-tumorigenic) mammary epithelial cell lines (184A1), the extract of normal breast tissue, are shown in lanes B and C respectively. $^{125}$I-labelled lysate of 184A1 and extract of normal breast tissue were also subjected to immunoprecipitation with the antibody that was preabsorbed with the immunogen are shown in lanes D and E respectively. Molecular weight standards are shown in lane A.

The antibody was purified and used for subsequent study. Double immunodiffusion studies with goat antibodies to subclass of mouse immunoglobulin revealed that anti-LEA.135 antibody is an $IgG_1$ immunoglobulin with a kappa-light chain.

One clone, the supernatant of which showed the greatest evidence of binding to normal breast cells during the screening procedure, were selected for production of antibody in greater quantities. The hybrid cells, designated A 56.7C2 were injected i.p. into BALB/c nude mice which had been primed 4 weeks earlier with pristane (0.5 ml/mouse via i.p.). Two to 3 weeks later, ascites was harvested from the mice and clarified by centrifugation at 12,000×g and 4° for 15 min. The immunoglobulin was precipitated from the ascites by the addition of an equal volume of saturated solution of ammonium sulphate, adjusted to PH 7.0. The solution was mixed gently at 4° for 2 hr. The precipitate was collected by centrifugation of the solution at 12,000×g for 15 min dissolved in PB to the original volume of the ascites fluid, and dialyzed extensively against the same buffer. The dialyzed material was applied to a column (1.8×17cm) containing DE-52 which had been equilibrated with PB. Following the application of sample, the column was washed with PB, and the immunoglobulin was eluted with the buffer containing a gradient of 5 to 100 mM NaCl. Two-ml fractions were collected, and the $A_{280}$ of each was measured on a spectrophotometer. The amounts of human lgG in fractions were determined by the enzyme-linked immunosorbent assay. The fractions containing human lgG were pooled, dialyzed against several changes of PBS, concentrated, and stored at –20°. The screening process also revealed that the epitope recognized by anti-LEA.135 antibody is resistant to formalin-fixation and paraffin-embedding procedures.

The morphological preservation utilizing frozen tissue is very much dependent upon careful handling of the samples. The tissue samples are sliced in small cubes (3–5 $mm^3$), washed with phosphate buffered solution (PBS), covered with OCT tissue-embedding medium (Lab-Tek Division, Miles Laboratories, Inc., IL), wrapped in aluminum foil, snap frozen in liquid nitrogen for 4–5 min, and finally stored at –70° C. until used. The tissue, thus processed, is sectioned (5–8 μm in thickness), collected on gelatin-coated glass slides, dried preferably in the vacuum chamber of a lyophilizer apparatus for 6–12 hr, fixed in acetone for 10 sec to 10 min and finally air dried. The duration of fixation of tissue antigen with acetone should be determined empirically, as some antigens do not survive the usual 10-min fixation. The section can be either immediately immunostained or stored at –20° C. The details of freezing and processing of tissue samples and the preservation of tissue antigen have been described at great length [H. Stein et al., "Immunohistologic Analysis of the Organization of Normal Lymphoid Tissue and Non-Hodgkin's Lymphomas," J. Histochem. Cytochem 28:746–760 (1980); R. R. Tubbs et al., "Tissue Immunomicroscopic Evaluation of Monoclonality of B-cell Lymphomas: Comparison With Cell Suspension Studies," Am. J. Clin. Pathol. 76:24–28 (1981); S. Poppema et al., "Distribution of T Cell Subsets in Human Lymph Nodes," J. Exp. Med. 153:30–41 (1981); R. Warnbe et al., "Tissue Section Immunologic Methods in Lymphomas".)

Surprisingly high numbers of antigens have been shown to retain their antigenicity despite the use of denaturing reagents and exposure to high temperatures during the fixation and embedding of tissue in paraffin wax. However, fixation does irreversibly affect (denature or "mask") some antigens such that they cannot be recognized by their corresponding antibodies. A variety of fixatives have been used, including buffered formalin, B-5, Bouin's, and Zenker's. As a rule, tissue should be fixed for a minimum length of time consistent with obtaining good morphological appearance. The most commonly used fixative is buffered formalin, as it is easy to prepare and has excellent preservation of tissue structure. The tissue should be sectioned into small blocks and fixed with a freshly prepared and buffered solution of formaldehyde at room temperature for 1–2 hr (or less if possible). Following fixation, the tissue should be washed and kept in 90% (vol/vol) alcohol until processed to paraffin blocks at the earliest opportunity. Cell smears and tissue imprints may be fixed by treating them briefly with methanol or buffered formal acetone (D. Y. Mason et al., "The detection of intracellular antigens in human leucocytes by Immunoperoxidase Staining," Br. J. Haematol. 31:361–370 (1975)].

Figure 2:
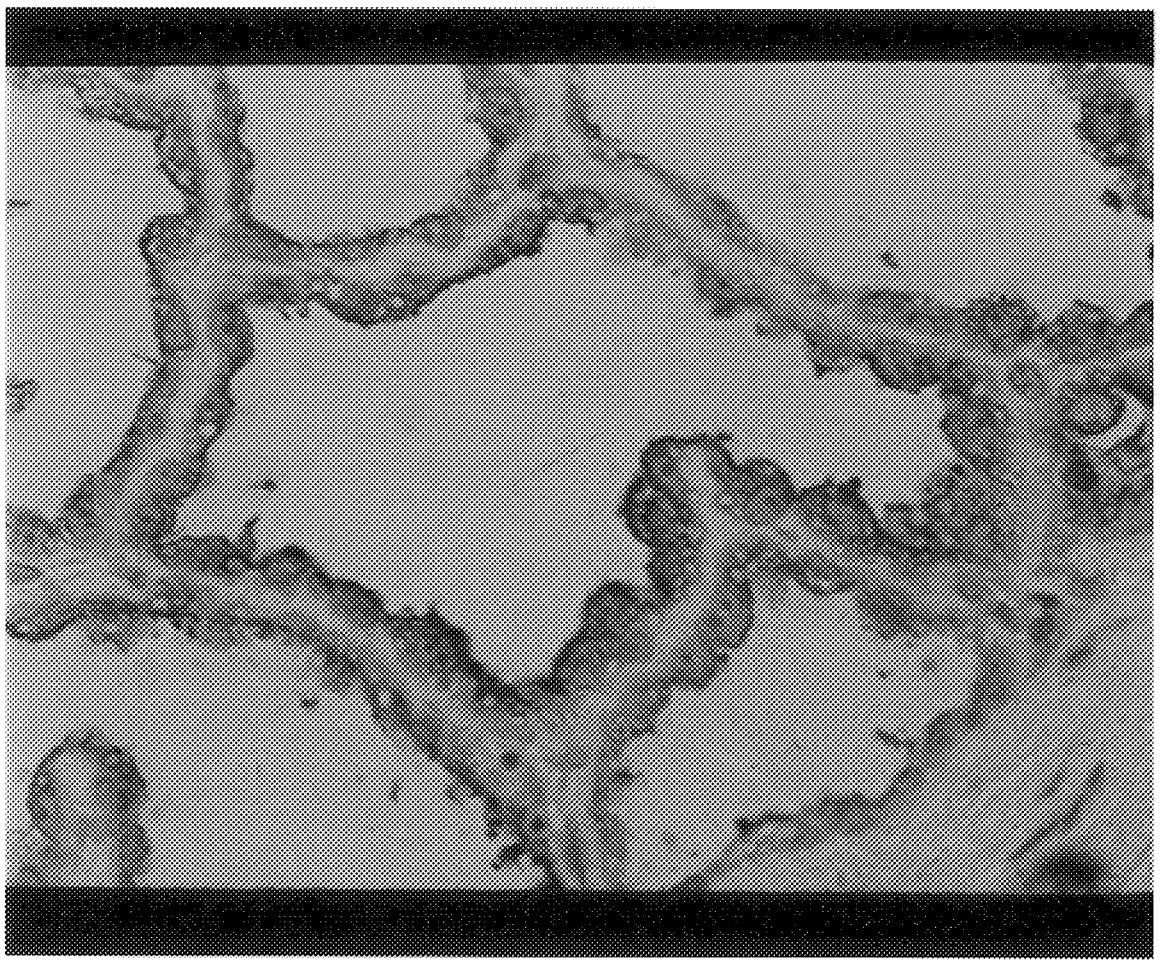
FIG. 2 illustrates the binding pattern of anti-LEA.135 antibodies to normal mammary epithelial cell lines.

The chief parameters for selection of anti-LEA.135 antibody were its ability to react with normal mammary epithelial cell (MEC) lines and the absence of reactivity for invasive and metastatic malignant counterparts in the tissue sections. In normal breast tissues, LEA.135 was expressed predominantly on the apical plasma membrane of luminal epithelial cell lines lining the ducts (FIG. 2). FIG. 2 shows the binding pattern of anti-LEA.135 monoclonal antibody to mammary epithelial cell lines in formalin-fixed and paraffin-embedded tissue sections by an indirect immunohistological staining method. The sections were counterstained with Mayer's hematoxylin. The stromal components were consistently negative. The antibody exhibited a homogeneous and predominant reactivity with apical plasma membrane of the lactating mammary epithelial cell lines (original magnification ×200). In benign breast diseases (such as fibroadenoma or hyperplasia), as in normal breast, expression of LEA.135 was exhibited. In contrast, metastatic mammary carcinoma cells of infiltrating ductal and lobule in regional lymph node, liver or lung showed no detectable expression of LEA.135.

Figure 3:
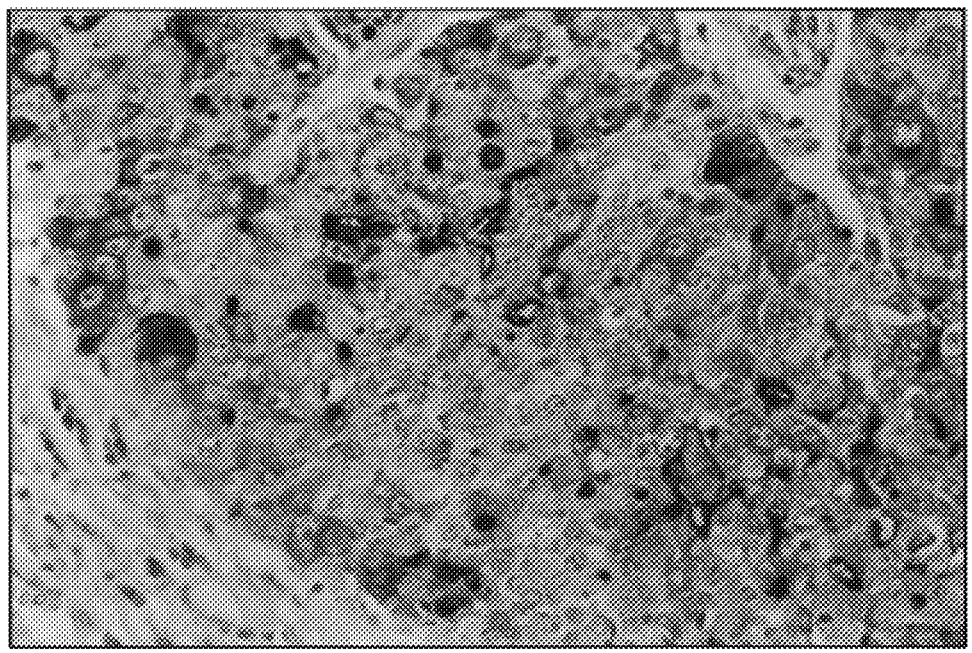
FIG. 3 illustrates the binding pattern of anti-LEA.135 antibodies to malignant mammary epithelial cell lines.

FIG. 3 shows the reactivity on anti-LEA.135 antibody with malignant mammary epithelial cell lines in paraffin-fixed tissue sections by an indirect immunohistochemical staining method. Malignant mammary epithelial cell lines from a patient with good prognosis (survival >5 years) showed reactivity heterogeneously. The connective tissue cells were consistently negative (original magnification 300×). The section were counterstained with Mayer's hematoxylin. The results suggest the use of LEA.135 assay as a favorable prognostic marker for mammary carcinomas.

The invention may be better understood with reference to the accompanying example, which is intended to be illustrative only and should not be viewed as in any sense limiting the scope of the invention, which is defined hereinafter in the accompanying claims.

EXAMPLE

A retrospective investigation was carried out to investigate the prognostic value of LEA.135 expression in 40 cases with 5 to 15 years of follow-up of patients with primary breast carcinomas.

Materials and Methods

Patients

Tissue sections were obtained from the University of California (Davis) Medical Center, Sacramento, Calif. The following data were obtained by chart review of corresponding patients: age and tumor stage at the time of biopsy, quantitative estrogen receptors status, nodal status, histological subtype and time to progression in years (defined as tumor recurrence, progression, or cancer-related death) or overall survival (O.S.) for those who didn't progress. Duration of O.S. was determined by using the date of the last visit to clinic recorded in the chart.

Histological Evaluation

Tissue sections, stained with hematoxylin and eosin were evaluated independently of the immunostaining readings for histopathological type, nuclear grade (NG) and morphological differentiation. Immunostained sections were reviewed by three independent pathologists who were blinded to status of patients. The heterogeneity in the intensity of staining of tumor cells within samples, although infrequently noted, was not included in the determination of the score.

Statistical Analysis

Initially, univariate analyses were performed where the association with overall survival (O.S.) was examined for each of the following prognostic factors that included morphological differentiation, age, ploidy, axillary lymph node involvement and estrogen receptor status. For each of these factors, Kaplan-Meier curve was drawn and log-rank test was performed. To determine whether LEA.135 expression independently contributed significant prognostic information above and beyond the established factors, a stratified log-rank test was performed with O.S. as the outcome and LEA.135 expression as the predictor of interest with morphological differentiation, age, ploidy, axillary lymph node involvement and estrogen receptor status as the stratification variable.

Preparation and Staining of Tissue Sections

Normal and neoplastic human tissues were obtained from the surgical pathology files of Los Angeles County/University of Southern California or University of California, Davis, Calif. Tissue used were either frozen in liquid nitrogen or fixed in formalin. Tissues were sectioned at 5 microns and representative sections were stained with hematoxylin and eosin to confirm the diagnosis prior to immunostaining. Staining observed in frozen and formalin-fixed, paraffin-embedded sections was similar quantitatively and qualitatively, leading to a preference in the latter, because of superior morphology and also for performing retrospective study. One hundred $\mu l$ of the antibody (1 $\mu g/ml-1$) were applied directly to cytocentrifuge preparation of cell lines or tissue sections. Otherwise the immunohistochemical method was as described previously. The primary antibody preabsorbed with the immunogen (an extract of normal breast tissue) served as a negative control.

Comparison of Epitopes

Figure 4:
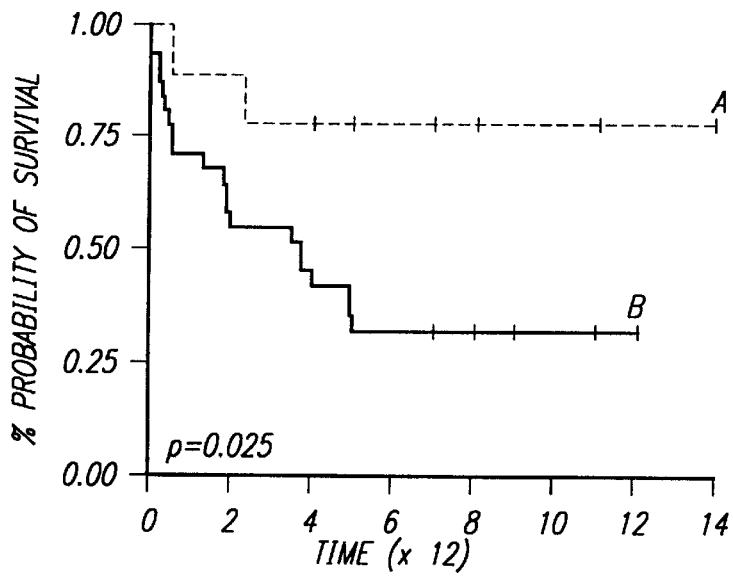
FIG. 4. Kaplan-Meier plot of disease progression in patients whose tumor cells were LEA.135-positive (A, score=2; N=9) versus LEA.135-negative (B, score=0; N=31). Time was measured from biopsy to last follow-up in year.

Competitive immunocytochemically steric-inference assays were performed using immunocytological techniques in order to compare the nature of the epitopes recognized by anti-LEA.135 antibody to those by previously reported antibody in relation to human mammary epithelial cell lines. The freshly-frozen sections of breast tissue containing normal MEC were incubated first with the unlabelled test antibodies that included EMA, milk-fat-globule membrane glycoprotein (MFGM-gp70), MFGM-gp155, human milk-fat-globule 1 (HMFG-1), HMFG-2 and pan keratin, and receptor for epidermal growth factor followed by incubation with predetermined concentration of biotinylated anti-LEA.135 antibody. The remainder of the staining procedure was as described previously. Any change in the intensity of staining with reference to control preparations was recorded.
Results In normal breast tissues, LEA.135 was expressed predominantly on the apical plasma membrane of luminal epithelial cell lines lining the ducts (FIG. 2). In benign breast diseases, such as fibroadenoma or hyperplasia, as in normal breast, expression of LEA.135 was exhibited. In a retrospective study of 40 cases of primary breast carcinomas, expression of LEA.135 independently correlated with a favorable prognosis (FIG. 3, FIG. 4). A comparison of overall survival (O.S.) was made of patients whose tumor cells exhibited immunoreactivity with anti-LEA.135 antibody compared with those whose specimens showed absence of LEA.135 expression. A statistically significant univariate association between LEA.135 expression and O.S. was observed (log-rank p=0.025).

Figure 5:
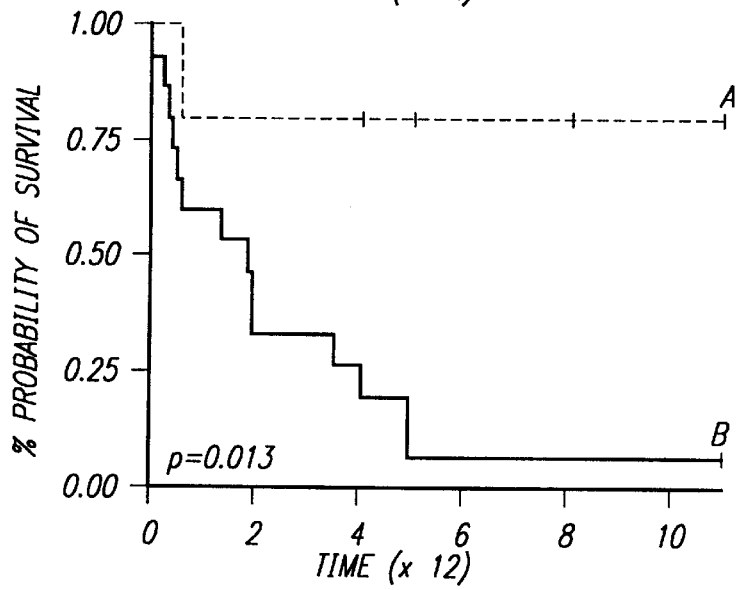
FIG. 5. Kaplan-Meier plot of disease progression in patients whose tumor cells were morphologically poorly differentiated and LEA.135-positive (A, score=2; N=5) versus LEA.135-negative (B, score=0; N=15). Time was measured from biopsy to last follow-up in year.
Figure 6:
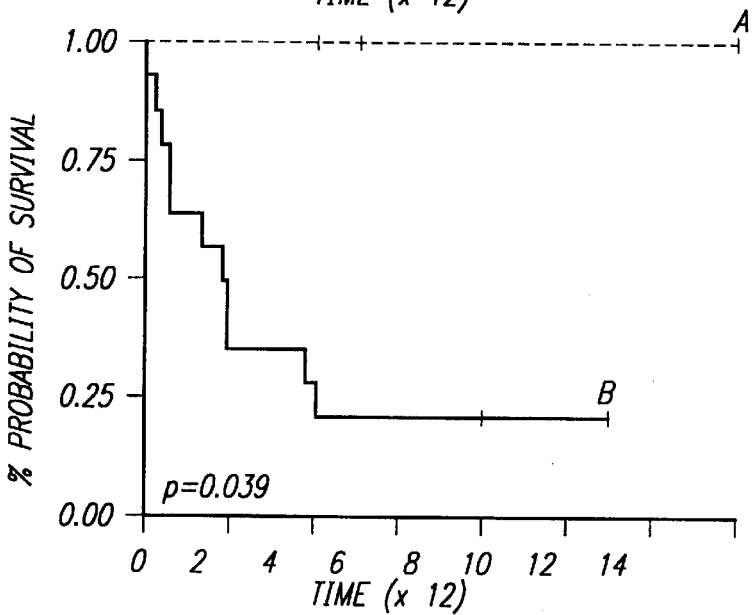
FIG. 6. Kaplan-Meier plot of disease progression in patients whose tumor cells were aneuploid and LEA.135-positive (A, score=2; N=3) versus LEA.135-negative (B, score=0; N=14). Time was measured from biopsy to last follow-up in year.

Furthermore, patients with poorly differentiated and LEA.135-positive tumor cells have an improved survival (80%±0.179% at >5 years, p=0.013) than those with LEA.135-negative (07%±0.064% at >5 years) (FIG. 5). In addition, patients with aneuploid and LEA.135-positive tumor cells again exhibited a better prognosis (90%±0.001% at >5 years, p=0.039) compared with those with LEA.135-negative (21%±0.110% at >5 years) (FIG. 6). Interestingly, a subset of patients with well differentiated or diploid tumor cells or uninvolved axillary lymph nodes and LEA.135-positive showed a trend, although statistically insignificant, of an improved disease-free survival for more than 5 years compared with those with LEA.135-negative. comparison was made between epitopes recognized by anti-LEA.135 antibody with those of the previously described in relation to mammary epithelial cell lines. The immunoblocking assays showed that the antigenic binding site for anti-LEA.135 antibody was not blocked by other antibodies, suggesting that the epitope-recognized by anti-LEA.135 antibody is distinct (Table 1). Furthermore, the component recognized by anti-LEA.135 antibody is also different with respect to its molecular weight (results not shown).

In conclusion, the expression of LEA.135 appears to be associated with functional differentiation of mammary epithelial cell lines, hence a good prognosis.

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

TABLE 1

Comparison of epitopes detected by anti-LEA.135 and other known antibodies to epithelial antigens by an immunohistochemical steric-inference (blocking) assay.

| Initial incubation[a] (antibody to) staining[b] | Immunoperoxidase Second incubation | Intensity of labelling |
| --- | --- | --- |
| PBS[c] | Biotinylated anti-LEA.135 | ABC[d] + 3 |
| LEA.135 | Biotinylated anti-LEA.135 | ABC[d] — |
| MFGM-gp70 | Biotinylated anti-LEA.135 | ABC[d] + 3 |
| MFGM-gp155 | Biotinyiated anti-LEA.135 | ABC[d] + 3 |
| EMA | Biotinylated anti-LEA.135 | ABC[d] + 3 |
| HMFG-1 | Biotinylated anti-LEA.135 | ABC[d] + 3 |
| HMFG-2 | Biotinylated anti-LEA.135 | ABC[d] + 3 |
| Keratin | Biotinylated anti-LEA.135 | ABC[d] + 3 |
| EGF-R[e] | Biotinylated anti-LEA.135 | ABC[d] + 3 |

[a]Positive controls to demonstrate effective binding of antibody to MFGM-gp70, MFGM-gp155, epithelial membrane antigen (EMA), HMFG-1, HMFG-2, keratin and epidermal growth factor receptor were performed using the indirect immunoperoxidase method and the appropriate tissue sections and confirmed that each of these antibodies bound to target cells.
[b]Mean value for three different tissue sections utilized in this study.
[c]Phosphate buffered saline.
[d]Avidin-biotin-peroxidase complex.
[e]Epidermal growth factor receptor.

What is claimed:

1. An immortalized cell line which is ATCC deposit No. IIB11225.

2. A monoclonal antibody produced by a hybridoma HB 11225 as deposited with the A.T.C.C.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( v ) FRAGMENT TYPE: N-terminal ( x i ) SEQUENCE DESCRIPTION: SEQ ID NO:1:

```
Pro  Glu  Leu  Ser  Ala  Val  Tyr  Thr
 1                 5
```